(12) United States Patent
Itoh

(10) Patent No.: US 7,537,736 B2
(45) Date of Patent: May 26, 2009

(54) SAMPLING AND DISPENSING APPARATUS

(75) Inventor: Teruaki Itoh, Kumamoto (JP)

(73) Assignee: IDS Company, Ltd., Kumamoto-shi, Kumamoto (JP)

( * ) Notice: Subject to any disclaimer, the term of this patent is extended or adjusted under 35 U.S.C. 154(b) by 695 days.

(21) Appl. No.: 11/057,248

(22) Filed: Feb. 15, 2005

(65) Prior Publication Data
US 2005/0186119 A1 Aug. 25, 2005

(30) Foreign Application Priority Data
Feb. 19, 2004 (JP) ............................. 2004-043056

(51) Int. Cl.
*G01N 35/00* (2006.01)
(52) U.S. Cl. ........................... 422/100; 422/63; 422/99
(58) Field of Classification Search ................. 422/100, 422/67, 63, 99
See application file for complete search history.

(56) References Cited

U.S. PATENT DOCUMENTS

| 4,111,051 A | * | 9/1978 | Tamm et al. ............. 73/864.12 |
| 4,338,280 A | * | 7/1982 | Ambers et al. ............. 422/68.1 |
| 4,570,495 A | * | 2/1986 | Terada ..................... 73/864.25 |
| 4,632,808 A | * | 12/1986 | Yamamoto et al. ............ 422/72 |
| 4,927,603 A | * | 5/1990 | Fischer et al. ................. 422/67 |
| 5,032,361 A | * | 7/1991 | Kleinhappl et al. ........... 422/67 |
| 5,455,006 A | * | 10/1995 | Aota et al. ..................... 422/63 |
| 5,547,872 A | * | 8/1996 | Schalkowsky et al. ........ 436/49 |
| 5,695,721 A | * | 12/1997 | Kitagawa et al. ............. 422/99 |
| 5,744,729 A | * | 4/1998 | Tanaka .................... 73/864.25 |
| 6,274,092 B1 | * | 8/2001 | Itoh ........................... 422/104 |
| 6,387,327 B1 | * | 5/2002 | Ricci et al. .................... 422/72 |
| 2002/0064481 A1 | * | 5/2002 | Ishizawa et al. .............. 422/64 |

FOREIGN PATENT DOCUMENTS

JP          9-304398        11/1997

* cited by examiner

*Primary Examiner*—Jill Warden
*Assistant Examiner*—Monique Mirabeau
(74) *Attorney, Agent, or Firm*—Nixon & Vanderhye P.C.

(57) ABSTRACT

An apparatus main body which is arbitrarily elevated is provided in the middle of a guide rail which transports a test tube containing a blood specimen. A first movable base which turns around a first rotary shaft is provided at the apparatus main body, and a second movable base which turns around a second rotary shaft is provided on the first movable base. A pinch mechanism which pulls up the test tube and a sampling and dispensing probe which is retractably driven with respect to the test tube to sample the blood specimen inside the test tube are provided on the second movable base. When the blood specimen is sampled by the sampling and dispensing probe, the first movable base is turned to incline the test tube, and the second movable base is turned to incline the test tube with respect to the axis of the sampling and dispensing probe.

5 Claims, 4 Drawing Sheets

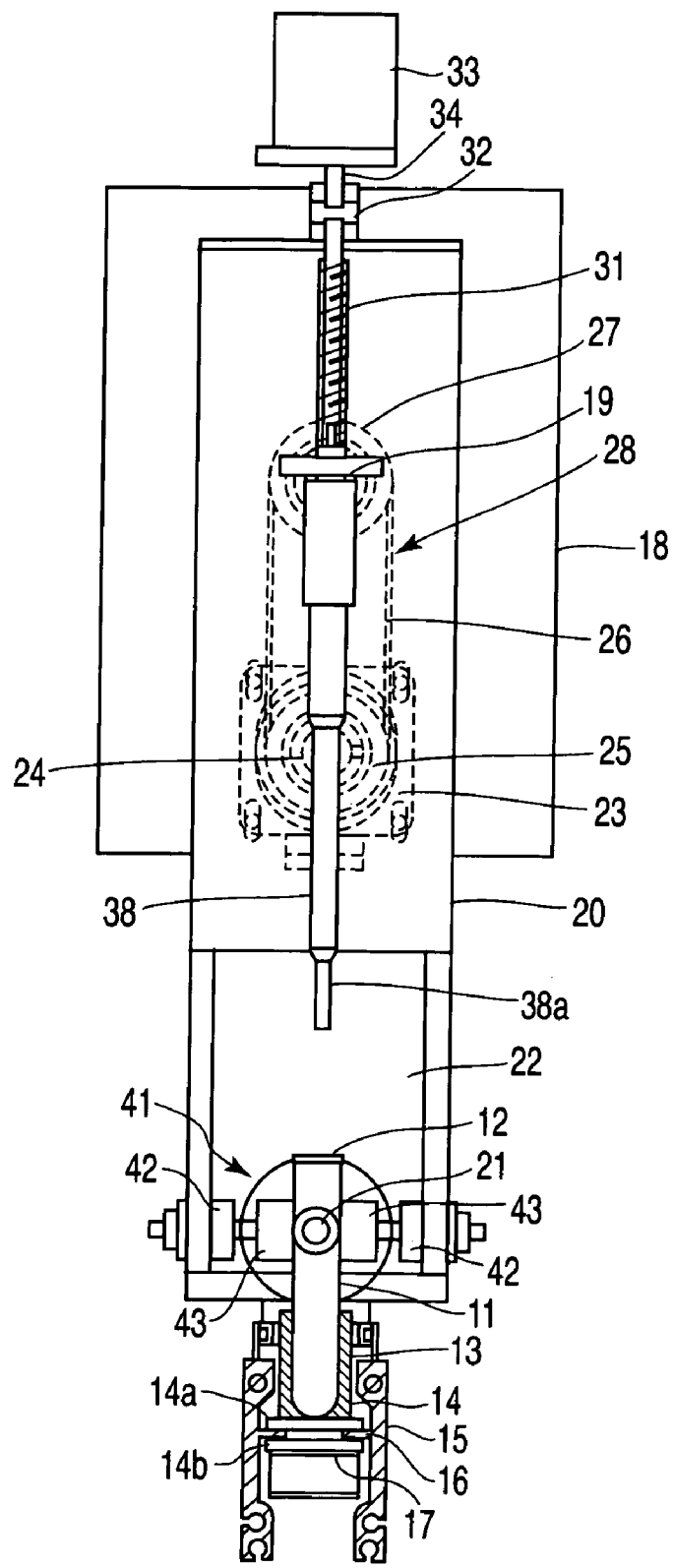
F I G. 2

SAMPLING AND DISPENSING APPARATUS

CROSS-REFERENCE TO RELATED APPLICATIONS

This application is based upon and claims the benefit of priority from prior Japanese Patent Application No. 2004-043056, filed Feb. 19, 2004, the entire contents of which are incorporated herein by reference.

BACKGROUND OF THE INVENTION

1. Field of the Invention

The present invention relates to a sampling and dispensing apparatus for automatically sampling and dispensing a blood specimen from a test tube for containing a blood specimen.

2. Description of the Related Art

In the case of carrying out a variety of blood inspections such as biochemical analysis, a test tube having a blood specimen contained therein is placed in a centrifugal separator, and a blood centrifugal separation process is carried out as preprocessing thereof. Next, sampling the blood serum contained in the test tube and dispensing the sampled blood specimen in a predetermined inspection container is carried out.

FIG. 5 is a view showing a general state of the blood specimen contained in the centrifugally separated test tube. Blood serum $\beta$ and a blood clot $\gamma$ are separated from each other inside a test tube 11. This separation is carried out by a separating agent $\delta$ such as silicon such that a boundary face between the blood serum $\beta$ and the blood clot $\gamma$ is clearly segmented. Namely, the centrifugally separated blood specimen is divided into three layers in order of the blood serum $\beta$, separating agent $\delta$, and blood clot $\gamma$ from the top part of the test tube 11.

Therefore, when the blood serum $\beta$ is sampled in the test tube 11 supported with an opening being upwardly set, a hollow, conically shaped sampling and dispensing probe formed in sharpened distal end shape is inserted from above the test tube 11, and only the blood serum $\beta$ is sampled by an air type suction mechanism (not shown). Next, the sampling and dispensing probe having the blood serum $\beta$ sampled therein is moved to a predetermined position, and the blood serum $\beta$ is dispensed relative to a predetermined inspection container.

However, the blood serum $\beta$ contained in the test tube 11 is extremely small in amount, and the distance from the liquid level to a bottom face (the top face of the separating agent $\delta$) is short. Moreover, irregularities may occur on the top face of the separating agent $\delta$, and the separating agent $\delta$ may be inclined. Therefore, when vacuum suctioning is carried out by the sampling and dispensing probe, a distal end opening of the sampling and dispensing probe abuts against the separating agent $\delta$, and the distal end opening is blocked. The blood serum cannot be sampled smoothly.

When the blood serum $\beta$ is vacuum-suctioned by the sampling and dispensing probe, it is known that a sampling auxiliary member having a flattening member at a distal end part of a shaft is inserted into the test tube 11, and the separating agent $\delta$ is pushed by the flattening member, thereby allocating a space for vacuum-suctioning the blood serum $\beta$ by the sampling and dispensing probe (for example, Jpn. Pat. Appln. KOKAI Publication No. 9-304398).

However, even if the separating agent $\delta$ contained in the test tube 11 is flattened by using the sampling auxiliary member as described above, the blood serum $\beta$ contained in the test tube 11 is extremely small in amount, and the distance from the liquid level to the bottom face (the top face of the separating agent $\delta$) is short. Therefore, there still persists a problem that, when vacuum-suctioning is carried out by the sampling and dispensing probe, the distal end opening of the sampling and dispensing probe abuts against the separating agent $\delta$, and the distal end opening is blocked, disabling smooth sampling.

BRIEF SUMMARY OF THE INVENTION

The present invention has been made in view of the foregoing circumstances. It is an object of the present invention to provide a sampling and dispensing apparatus capable of sampling blood serum contained in a test tube, even if it is extremely small in amount.

According to an aspect of the present invention, there is provided a sampling and dispensing apparatus comprising: a transport passage which transports a test tube containing a blood specimen while holding the test tube with a top opening thereof being oriented vertically upwardly; an apparatus main body allocated adjacent to the transport passage; a first movable base provided at the apparatus main body around a first rotary shaft in a vertical direction; a second movable base turnably provided around a second rotary shaft in a horizontal direction relative to the first movable base; a pinch mechanism provided on the second movable base to pinch a test tube to be transported on the transport passage and to pull up the test tube vertically upwardly from the transport passage; a sampling and dispensing probe provided on the first movable base to be retractably driven with respect to the test tube pinched by the pinch mechanism and to sample a blood specimen inside of the test tube; a first turnably driving mechanism which, when the blood specimen inside of the test tube is sampled by the sampling and dispensing probe, turns the first movable base and inclines the sampling and dispensing probe and the test tube with respect to a vertical direction; and a second turnably driving mechanism which, when the first movable base is turned by the first turnably driving mechanism, turns the second movable base, and further inclines the test tube with respect to an axle of the sampling and dispensing probe.

According to the present invention, there is attained the advantageous effect that a test tube is inclined during sampling, and the distance from the liquid level to the bottom face is increased, whereby smooth sampling can be carried out by a sampling and dispensing probe.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a side view showing the sampling and dispensing apparatus;

DETAILED DESCRIPTION OF THE INVENTION

Figure 1:
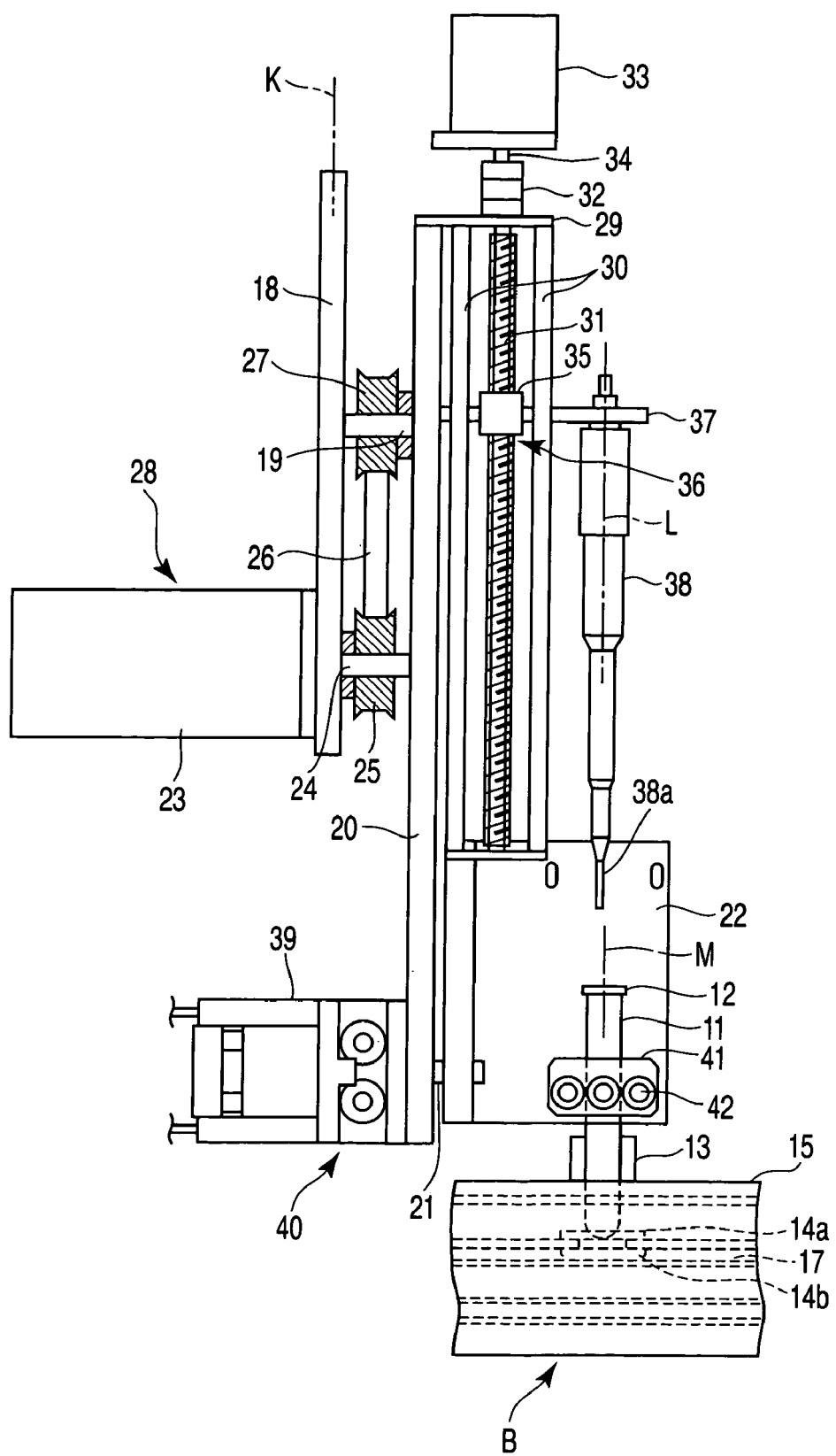
FIG. 1 is a front view showing a sampling and dispensing apparatus according to one embodiment of the present invention.
Figure 3:
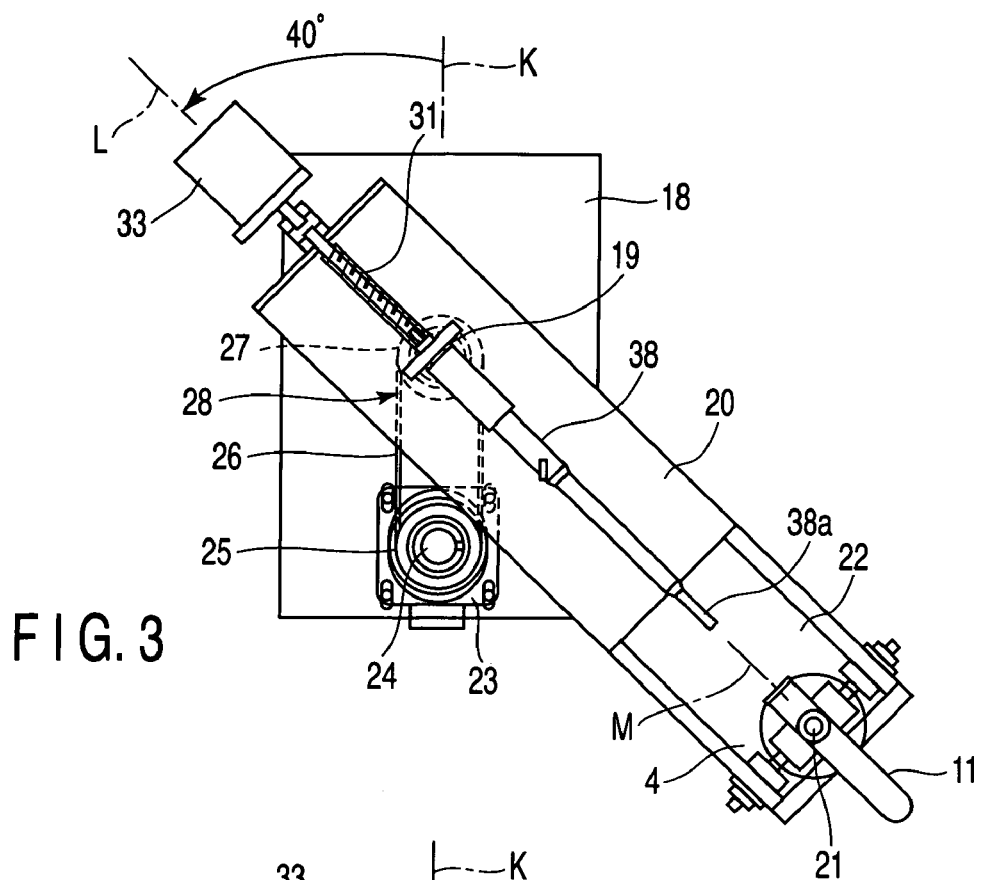
FIG. 3 is a side view showing an operation of the sampling and dispensing apparatus.
Figure 4:
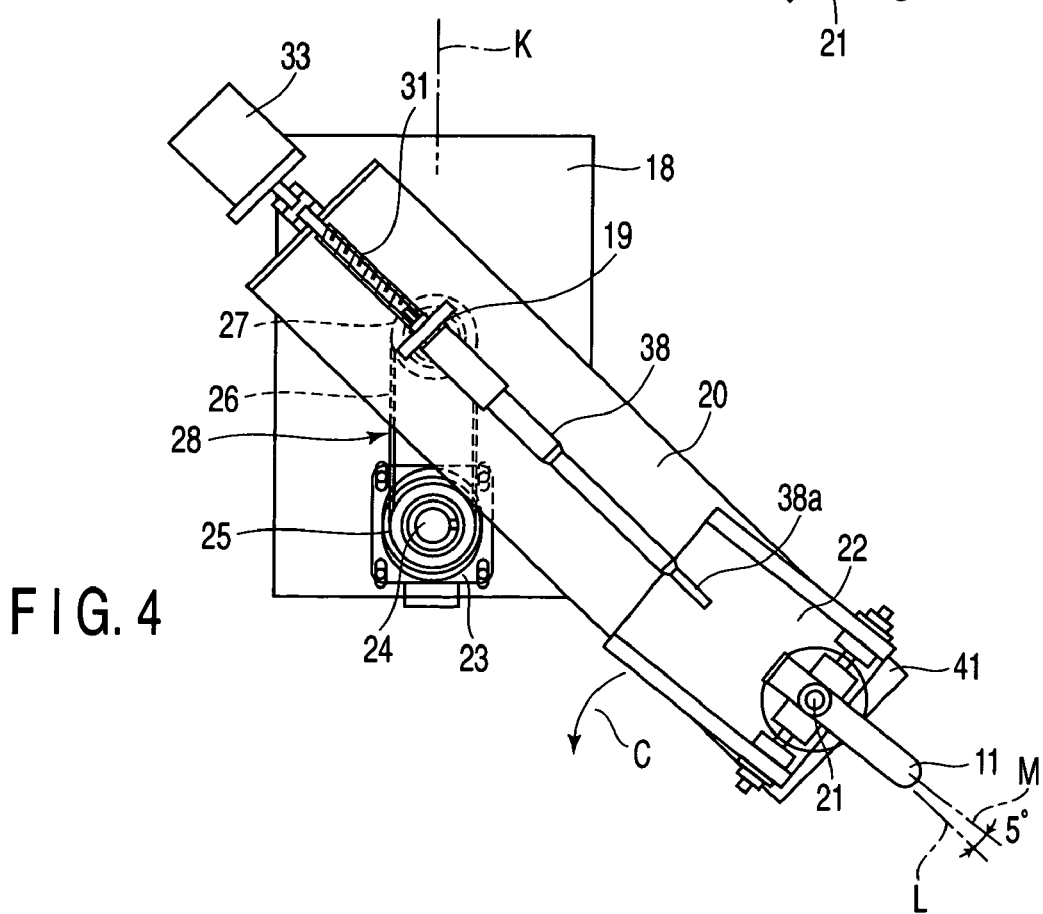
FIG. 4 is a side view showing an operation of the sampling and dispensing apparatus.
Figure 5:
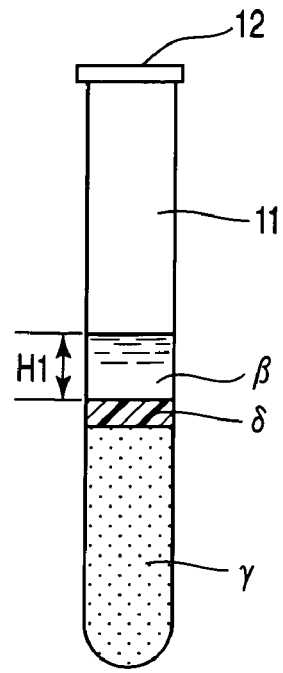
FIG. 5 is a side view showing a state of a test tube for use in the sampling and dispensing apparatus when its axial line is vertical.
Figure 6:
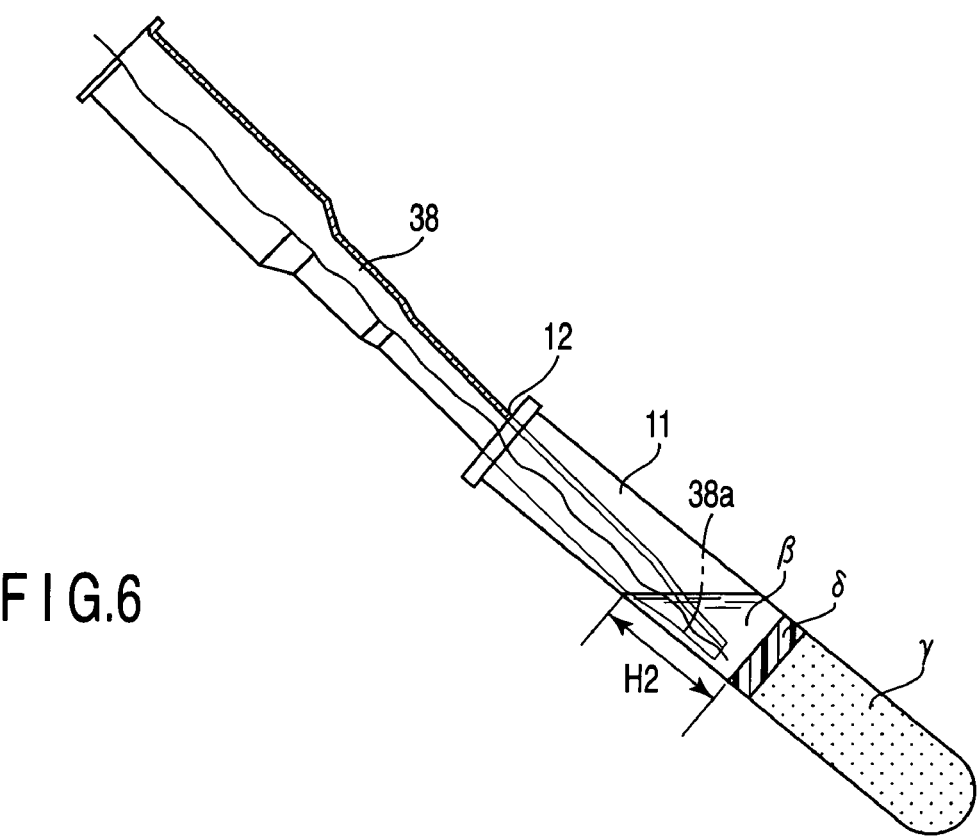
FIG. 6 is a side view showing a state of sampling from the test tube for use in the sampling and dispensing apparatus.

FIGS. 1 to 6 are views each showing one embodiment of the present invention. FIG. 1 is a front view showing a sampling and dispensing apparatus. FIG. 2 is a side view of the same apparatus. FIGS. 3 and 4 are side views each illustrating an operation of the same apparatus. FIG. 5 is a side view showing a test tube. FIG. 6 is a side view showing a state of sampling from the test tube.

A test tube 11 in the present embodiment is made of a transparent glass, as shown in FIGS. 5 and 6, and is formed in the cylindrical shape of a top opening 12. The blood specimen contained in this test tube 11 is centrifugally separated in advance, and blood serum $\beta$ and a blood clot $\gamma$ are separated from each other inside of the test tube 11. A boundary face between the blood serum $\beta$ and the blood clot $\gamma$ is separated by a separating agent $\delta$ such as silicon. Namely, the centrifugally separated blood specimen is divided into three layers in order of the blood serum $\beta$, separating agent $\delta$, and blood clot $\gamma$ from the upper part of the test tube 11.

As shown in FIGS. 1 and 2, the test tubes 11 are held by a test tube holder 13 on a one-by-one basis. The test tube holder 13 has a holder main body 14 molded of a synthetic resin material, for example. At the holder main body 14, an engagement portion is provided such that the test tubes are transported while they are held in a vertical state on a guide rail 15 serving as a transport passage. In the present embodiment, a ring shaped groove is provided between top and bottom two-stepped flange sections 14a and 14b.

As shown in FIG. 2, the guide rail 15 is a channel shape formed of a synthetic resin or an aluminum material, etc., and its cross section is formed in a U shape of a top opening. On the inside face of the guide rail 15, a guide rib 16 engaged with the ring shaped groove of the holder main body 14 is provided over the longitudinal direction of the guide rail 15. At the bottom part of the guide rail 15, a transport belt 17 composed of an endless belt is tensioned so as to travel freely. The bottom face of the test tube holder 13 held on the guide rail 15 comes into contact with the top face of the transport belt 17 so that the test tube holder 13 is transported by means of friction. The alternate long and short dashed line M shown in FIG. 1 indicates a reference axis of the test tube 11.

A sampling position B is provided in the middle of the guide rail 15. At the sampling position B, there is provided a sampling and dispensing apparatus for pinching the test tube 11 held on the test tube holder 13 and upwardly removing the tube.

Now, the sampling and dispensing apparatus will be described here. An apparatus main body 18 of the sampling and dispensing apparatus which is arbitrarily elevated relative to the guide rail 15 is provided above the guide rail 15. The alternate long and short dashed line K shown in FIG. 1 indicates a reference axis of the apparatus main body 18, and the reference axis K always indicates the vertical direction. The apparatus main body 18 is provided as one disk shaped body installed with its main face being defined in the vertical direction. This apparatus main body is configured so as to be elevated along the reference axis K by an elevating mechanism (not shown) such as an air cylinder.

A first movable base 20 which is turnable around a first rotary shaft 19 is provided at the apparatus main body 18. The first movable base 20 is provided as one disk shaped body installed parallel to the apparatus main body 18. A second movable base 22 which is turnable around a second rotary shaft 21 is provided at the lower end part of this first movable base 20. The first rotary shaft 19 and the second rotary shaft 21 are spaced in a vertical direction, and moreover, are parallel to each other.

A motor 23 such as a pulse motor is fixed to the apparatus main body 18 while a rotary shaft 24 of the motor is defined in a horizontal direction. A drive pulley 25 is engagingly fitted to the rotary shaft 24, so that the drive pulley 25 is designed to transmit rotation to a follower pulley 27 engagingly fitted to the first rotary shaft 19 via a belt 26. In addition, the first rotary shaft 19 is rotated by rotation of the motor 23, whereby the first movable base 20 can be turned and inclined up to substantially 45 degrees relative to the vertical axis. That is, a first turnably driving mechanism 28 is composed of the motor 23, the drive pulley 25, the follower pulley 27, and the first movable base 20.

At the upper end part of the first movable base 20, two guide rods 30 and one screw shaft 31 are provided parallel to the main face of the first movable base 20 via a bracket 29. The upper end part of the screw shaft 31 is linked with a rotary shaft 34 of a servo motor 33 via a coupling 32. A nut 35 is helically fitted to the screw shaft 31, and a ball screw 36 is formed. A support member 37 elevated and guided by the guide rod 30 is provided at the nut 35, and a sampling and dispensing probe 38 for sampling the blood specimen inside the test tube 11 is provided at the support member 37. The alternate long and short dashed line L shown in FIG. 1 indicates a reference axis of the sampling and dispensing probe 38.

The sampling and dispensing probe 38 is formed in a hollow, conical shape which forms a shape such that a distal end part 38a is acutely sharpened. The sampling and dispensing probe 38 is connected to a vacuum suctioning source (not shown) via a tube. In addition, the distal end part 38a of the sampling and dispensing probe 38 is inserted into the test tube 11 through the top opening 12 of the test tube 11 so that the blood serum $\beta$ can be sampled.

A second turnably driving mechanism 40 is configured such that a rotary actuator 39 for rotationally driving the second rotary shaft 21 is provided at the lower end part of the first movable base 20, and that the second movable base 22 is inclined by substantially about 5 degrees relative to the first movable base 20 around the second rotary shaft 21.

A pinching mechanism 41 for pinching the test tube 11 is provided at the second movable base 22. The pinching mechanism 41 composed of a pair of pinch pieces 43 opened and closed by the air cylinder 42 so that a bellows of the test tube 11 can be pinched between both sides. Therefore, when the apparatus main body 18 rises in a state in which the test tube 11 is pinched by a pair of pinch pieces 43, the test tube 11 is sampled and pulled up from the test tube holder 13.

Now, a functional description will be given with respect to the sampling and dispensing apparatus configured as described previously.

The blood specimen contained in the test tube 11 is centrifugally separated in advance. The blood serum $\beta$ and the blood clot $\gamma$ are separated from each other inside of the test tube 11, and the boundary face between the blood serum $\beta$ and the blood clot $\gamma$ is separated by the separating agent $\delta$ such as silicon. The test tubes 11 each containing this blood specimen are held in a vertical state by the test tube holder 13 on a one-by-one basis while the top opening 12 is oriented upwardly, and are transported by the transport belt 17. Thus, the test tube holder 13 is transported along the guide rail 15. At this time, a reference axis M indicates a vertical direction.

When the test tube 11 is set at the sampling position B, the apparatus main body 18 of the sampling and dispensing apparatus is lowered. Then, when the pair of pinch pieces 43 of the pinching mechanism 41 are opposed to the bellows of the test tube 11 to be pinched by the pair of pinch pieces 43, the pair of pinch pieces 43 are closed to pinch the test tube 11 by the air cylinder.

Next, when the apparatus main body 18 rises, the test tube 11 is sampled from the test tube holder 13. That is, the test tube 11 and the test tube holder 13 are separated from each other, and only the test tube 11 is pulled up.

When the test tube 11 is pinched by the pinch mechanism 41, and then, is pulled up to a predetermined height, the motor 23 is driven. Then, rotation of the rotary shaft 24 is dynamically transmitted sequentially to the drive pulley 25, the belt 26, and the follower pulley 27, and the first rotary shaft 19 rotates. Therefore, the first movable base 20 turns around the first rotary shaft 19, and is inclined by 40 degrees to the vertical axis, as shown in FIG. 3. Then, the sampling and dispensing probe 38 provided at the first movable base 20, the rotary actuator 39 configuring the second turnably driving mechanism 40, and the test tube 11 pinched by the pinch mechanism 41 are integrally inclined by 49 degrees. That is, a reference axis L and the reference axis M are inclined by 40 degrees with respect to the reference axis K.

Next, when the rotary actuator 39 is driven to rotate the second rotary shaft 21, the second movable base 22 is turned around the second rotary shaft 21. Then, the second movable base 22 is inclined by substantially 5 degrees in the direction indicated by the arrow C of FIG. 4 with respect to an axis of the first movable base 20. Therefore, the test tube 11 is inclined by substantially 5 degrees in the direction indicated with respect to an axis of the sampling and dispensing probe 38. That is, the reference axis M is inclined by 45 degrees with respect to the reference axis K, and the reference axis M is inclined by 5 degrees with respect to the reference axis L.

Therefore, assuming that the distance between the liquid level of the blood serum β and the separating agent δ contained in the test tube 11 is H1 in a vertical state shown in FIG. 5, and is H2 when the reference axis M is inclined by 45 degrees as shown in FIG. 6, a relationship of H1<H2 is established. The liquid level of the serum β is separated from the separating agent δ by inclining the test tube 11.

Next, when the servo motor 33 is driven, the screw shaft 31 of the ball screw 36 rotates, and a rotational movement is converted into a linear movement by the nut 35 spirally fitted to this screw shaft 31. Therefore, the sampling and dispensing probe 38 supported by the nut 35 via the support member 37 is lowered, and its distal end part 38a is inserted into the test tube 11. At this time, the reference axis M of the test tube 11 is inclined by substantially about 5 degrees with respect to the reference axis L of the sampling and dispensing probe 38. Thus, as shown in FIG. 6, the distal end part 38a of the sampling and dispensing probe 38 is inserted into the deepest portion of the serum β. That is, a space is allocated when the serum β is vacuum-suctioned by the sampling and dispensing probe 38, the blood serum β can be sampled without being left in the test tube 11, and the amount of sampling can be increased.

As described above, the sampling and dispensing apparatus according to the present embodiment provides the advantageous effect that the test tube is inclined during sampling, and the distance from the liquid level to the bottom face is increased, whereby smooth sampling can be carried out by the sampling and dispensing probe.

Although the turnable driving mechanism has been designed to transmit rotation of the pulse motor or the rotary actuator to the rotary shaft, the turnable driving mechanism may be an air cylinder, a rack-and-pinion mechanism and the like without being limited thereto.

In addition, although a description has been given with respect to a case in which the blood specimen contained in the test tube is centrifugally separated in advance, the blood serum and the blood clot are separated from each other inside the test tube, and only the blood serum is sampled, the present invention can be applied to a case of sampling the blood specimen before centrifugally separated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sampling and dispensing apparatus comprising:
   a transport passage which transports a test tube containing a blood specimen while holding the test tube with a top opening thereof being oriented vertically upwardly;
   an apparatus main body allocated adjacent to the transport passage;
   a first movable base provided at the apparatus main body around a first rotary shaft;
   a second movable base turnably provided around a second rotary shaft, the second rotary shaft being spaced from the first rotary shaft in a vertical direction;
   a pinch mechanism provided on the second movable base to pinch a test tube to be transported on the transport passage and to pull up the test tube vertically upwardly from the transport passage;
   a sampling and dispensing probe provided on the first movable base to be retractably driven with respect to the test tube pinched by the pinch mechanism and to sample a blood specimen inside of the test tube;
   a first turnably driving mechanism which, when the blood specimen inside of the test tube is sampled by the sampling and dispensing probe, turns the first movable base and inclines the sampling and dispensing probe and the test tube with respect to the vertical; and
   a second turnably driving mechanism which, when the first movable base is turned by the first turnably driving mechanism, turns the second movable base, and further inclines the test tube with respect to an axis of the sampling and dispensing probe.

2. A sampling and dispensing apparatus according to claim 1, wherein the first turnably driving mechanism is composed of a motor provided at the apparatus main body and a power transmission mechanism which transmits rotation of the motor to the first rotary shaft.

3. A sampling and dispensing apparatus according to claim 1, wherein the second rotatably driving mechanism is a rotary actuator provided on the first movable base.

4. A sampling and dispensing apparatus according to claim 1, wherein the sampling and dispensing probe is retractably driven by a motor provided on the first movable base and a ball screw driven by the motor.

5. A sampling and dispensing apparatus according to claim 1, wherein the inclination angle by the first turnably driving mechanism is 40 degrees and the inclination angle by the second turnably driving mechanism is 5 degrees.

* * * * *